United States Patent [19]

Herriott

[11] Patent Number: 5,566,679
[45] Date of Patent: Oct. 22, 1996

[54] METHODS FOR MANAGING THE REPRODUCTIVE STATUS OF AN ANIMAL USING COLOR HEAT MOUNT DETECTORS

[75] Inventor: Kevin S. Herriott, Meridian, Id.

[73] Assignee: Omniglow Corporation, Novato, Calif.

[21] Appl. No.: 297,972

[22] Filed: Aug. 31, 1994

[51] Int. Cl.⁶ .................................................. A61B 10/00
[52] U.S. Cl. ............................................................ 128/738
[58] Field of Search .................................. 128/738, 774; 119/174

[56] References Cited

U.S. PATENT DOCUMENTS

| | | | |
|---|---|---|---|
| 3,076,431 | 2/1963 | Rule et al. | 119/1 |
| 3,158,134 | 11/1964 | Larson | 119/1 |
| 3,942,475 | 3/1976 | Wassilieff | 119/1 |
| 4,206,766 | 6/1980 | Bielka | 128/738 |
| 4,239,018 | 12/1980 | Griffin et al. | 119/1 |
| 4,635,587 | 1/1987 | Leonardo | 119/1 |
| 4,696,258 | 9/1987 | Magrath et al. | 119/1 |
| 5,111,799 | 5/1992 | Senger et al. | 128/738 |

Primary Examiner—Max Hindenburg
Attorney, Agent, or Firm—Majestic, Parsons, Siebert & Hsue

[57] ABSTRACT

An apparatus and method for indicating the onset of behavioral estrus in cattle. The apparatus is comprised of a base element with a plurality of chemical containing receptacles located on top of the base, with those receptacles being housed inside a cover which is attached to the base and enclosing the receptacles. The receptacles are pressure responsive and contain a chemiluminescent indicator. When the receptacles are discharged in response to the pressure, the chemicals are released from the receptacles and comingle and chemically react to emit light as a result of a peroxyoxalate chemiluminescent reaction. The detection patch is manufactured in a selection of colors in the management method of this invention, with each color designating a particular breeding management status for a cow. The detection apparatus is applied to the cow, which is then monitored for release of the indicator in the patch. When discharged receptacles are observed, the cows are then treated as designated by the color patch which the cow is wearing.

12 Claims, 1 Drawing Sheet

METHODS FOR MANAGING THE REPRODUCTIVE STATUS OF AN ANIMAL USING COLOR HEAT MOUNT DETECTORS

BACKGROUND OF THE INVENTION

1. Technical Field

This invention relates to cows, more specifically to a method and apparatus for detecting heat and managing breeding in cows.

2. Background

Commercial raising of cattle for either beef or dairy production requires proper management. In addition to the various husbandry concerns such as herd health and nutrition, a critical management area for economic survival of any cattle operation, is the breeding management of the cows, in the case of beef cows without successful breeding, there are no calves produced and therefore no product to sell. In the case of dairy cows, the cows will not produced milk unless they have a calf, which is again dependent upon successful breeding management.

While breeding management is important in any cattle operation, the timing of breeding and breeding intervals are generally more critical in dairy operations. Dairy cows are managed more intensely and often bred exclusively by artificial insemination. In natural matings, a bull will service a cow numerous times during each fertile receptive cycle. With artificial insemination, the object is to inseminate the cow the minimum number of times possible to insure pregnancy during that fertile cycle. There are costs associated with both each unit of semen used on the cow, as well as increased labor costs with increased numbers of matings; this is why it is important to both minimize the number of inseminations and yet still have a high probability of the cow becoming pregnant.

A basic understanding of fertility and the estrous cycle of the cow is necessary for appreciation of existing management problems and solutions. The estrous period in cattle occurs approximately every 21 days in non-pregnant or open cows. The cow then remains in estrus for approximately 12–24 hours. The cow ovulates approximately 14 hours after estrus. The time of ovulation is the optimum time for artificial insemination. If the cow is successfully inseminated, she will become pregnant for approximately 280 days. Dairy cows are managed such that they are ideally bred and become pregnant again 45 to 60 days after calving. The dairy cows are preferably maintained pregnant to insure milk production.

If the desired estrous cycle, for example, the first postpartum estrous cycle, is not detected or if the cow is not successfully bred during a particular cycle, the cow cannot be bred for at least another 21 days. It is estimated that for every day past a set goal date that a cow remains open, there is an economic loss of between $1.00–$3.00 per day. An average sized dairy herd is between 200 to 1,000 cows. If the 24 hours during which the cow should be bred is missed for each cow, this represents an economic loss of $4,200.00 to $21,000.00 annually. Often cows are not successfully bred for as many as 3 estrous cycles, due to infertility, infections and semen-related problems. If one half of the cows in a herd of 200 to 1,000 is not impregnated for 3 cycles, the estimated economic loss increases to $6,300.00 to $31,500.00 annually. These projections of economic loss to the producer demonstrate the critical importance of determination of the onset of estrus in cattle management.

A number of management techniques are used to detect estrus in cows. These techniques include rectal palpation of the cow's reproductive tract, tracking changes in the viscosity of the vaginal mucous discharge from the cow, and observing behavioral changes associated with estrus in cows.

Observing the behavioral changes of a cow in estrus is one of the most widely used management techniques and is used either alone or in conjunction with other techniques. During the fertile portion of a cow's estrous cycle, a cow will attempt to mount other cows and stand in place and allow other cows to mount and ride her. Likewise, when a cow is in estrus, other cows are stimulated to mount and ride her. Because of the short 12–24 hour duration of the time for breeding the cow, the cows must be observed at least twice a day in order to avoid having a fertile cycle go undetected. Most dairy cows are milked twice daily at 12-hour intervals. Many producers use this time of gathering the cows for the milking parlor to look for signs of cow-cow jumping and standing for mounting that are indicative of a cow in estrus. Observing the cows when they are gathered at milking time increases the likelihood of identifying the cows that are in good behavioral estrus. However, if the cows are uncomfortable or distracted at these times, for example, if the weather is too hot, cold or wet, or there is loud equipment operating nearby, the cows will not show signs of behavioral estrus at these easily observable milking times. Often the cows will wait until the cool part of the night to increase their activity levels, including mounting behaviors.

To aid in this detection of behavioral estrous, a number of aids have been developed. Rule et al., U.S. Pat. No. 3,026,431, and Larson, U.S. Pat. No. 3,158,134, both describe devices that are glued to the rump of a cow and show a change in appearance in response to the pressure applied to the devices by a mounting cow. Magrath, U.S. Pat. No. 4,696,258, shows a microencapsulated paint that is similarly applied to the cow's rump and changes appearance in response to the pressure of amounting cow. These devices have been found to have an incompatible shelf life with the management systems that utilize them. A similar device with a longer shelf life is Griffin et al., U.S. Pat. No. 4,239,018.

A problem with all of these devices is that they often are difficult to see. In many regions of the country during the winter, there are only 6–8 hours of day length. With short days lengths, one or both of the easily observable times for estrous detection at milking will be in the dark. Another factor that makes these devices difficult to see is that the color of the cow's body is sometimes in low contrast to the detection device.

A number of other devices exist that utilize electronic monitoring systems, such as Leonardo, U.S. Pat. No. 4,635,587, Senger et al., U.S. Pat. No. 5,111,799, and Bielka, U.S. Pat. No. 4,206,766. All of these electronic systems are generally not cost effective and have an increased likelihood of failure due to the increased number of parts and complexity.

Another problem with all of these systems is their inability to tell you the reproductive status of the cow other than that she has been mounted. In Wassileiff et al., U.S. Pat. No. 3,942,475 the use of a sleeve for removable replacement of differently colored indicators for facilitating color coding is disclosed. However, Wassileiff does not indicate a reason or method for use of the color coding.

To improve the breeding management of cows and decrease the economic losses associated with the nonpregnant interval it is important for the producer to be able to tell as much as possible about the cow when she is observed.

Other information, other than merely that the cow has been mounted, that is important for managing the cow includes whether or not the cow has been bred, whether or not the cow has been treated for infection or infertility and what should be done with the cow during the present estrous cycle. There are a number of management decisions to be made regarding a cow showing estrus such as whether she should be checked or treated for infertility because she has already been artificially inseminated and has had another cycle, the length of the particular cycle as an indication of cystic ovaries or early term abortion, and whether she should be treated therapeutically, culled or inseminated again and with what quality of semen.

What is still needed is a pressure responsive apparatus for detecting estrus in animals that exhibit estrous-related mounting behavior that can be more easily visualized and can also be seen in the dark.

What is also still needed is a method for managing the reproductive status of cows comprising using a plurality of different color pressure responsive estrous detection devices wherein each color, of device indicates a particular breeding management status for the cow.

DISCLOSURE OF INVENTION

The present invention is an apparatus and method for indicating the onset of behavioral estrus in cattle. The apparatus is comprised of a base element with a plurality of chemical containing receptacles located on top of the base, with those receptacles being housed inside a cover which is attached to the base and enclosing the receptacles. The receptacles are pressure responsive and contain a chemiluminescent indicator. When the receptacles are discharged in response to pressure, the chemicals are released from the receptacles and commingle and chemically react to emit light as a result of a peroxyoxalate chemiluminescent reaction.

The peroxyoxalate chemiluminescence of this invention can be formulated in any color. This invention includes a method for managing the reproductive cycle of the cow utilizing the estrus detecting apparatus. The management method utilizes the fact that the detection apparatus or patch can be manufactured in any color.

In the management method of this invention, the detection patch is manufactured in a selection of colors. Each color designates a particular breeding management status for a cow. The appropriate color patch is then selected from the colors available for the detection apparatus or patch. The estrus detection apparatus is then applied to the cow in the tail head or rump area. The cows to which the patches have been applied are then monitored for release of the indicator substance from the receptacles in the cover on the patch. The substances are discharged inside the cover in response to the pressure applied by a cow mounting the cow to which the patch is applied. Discharge of the patch indicates that the standing cow wearing the patch is showing behavioral estrous. When discharged receptacles are observed in the patch on the cow, the cows are then treated with the appropriate management scheme as designated by the color of detection apparatus or patch which the cow is wearing.

BEST MODE FOR CARRYING OUT INVENTION

Figure 1:
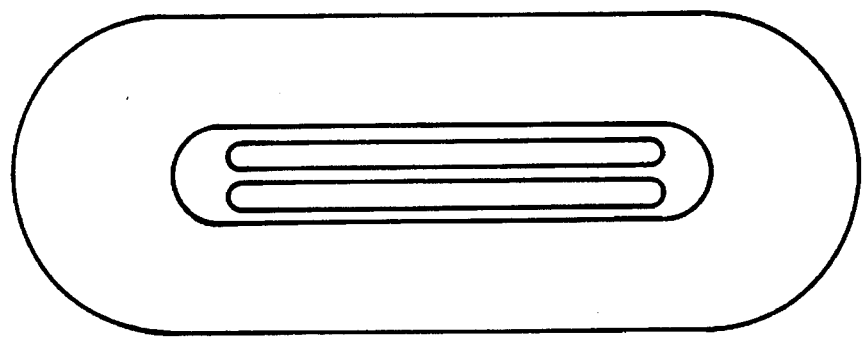
FIG. 1 is a top view of the preferred embodiment of the present invention.

The present invention generally comprises an apparatus and method for indicating the onset of behavioral estrus in cattle. Referring now to FIG. 1, the apparatus is in the shape of elliptical patch 10. Patch 10 is comprised of base 12. Base 12 has bottom surface 14 and top surface 16. A plurality of receptacles, here pair 18 and 19 are located on top of base 12, with receptacles 18 and 19 being housed inside cover 24, which is attached to base 12.

Figure 2:
FIG. 2 is a side view of the present invention showing the relationship and placement between the base, the receptacles, dispersing member and cover.

Base 12 can be made from any suitable material, such as a flexible plastic, a woven synthetic, or a fabric treated to improve its wearability; for example, by waterproofing the fabric. In the preferred embodiment, base 12 is made of canvas and has a self-adhesive coating on bottom 14 and a water repellent treatment on top surface 16. Receptacles 18 and 19 are located on top surface 16 of patch 10, in the center of patch 10, as seen in FIG. 1. In the preferred embodiment, patch 10 possesses a pair of receptacles 18 and 19, which are manufactured from plastic. Receptacles 18 and 19, collectively contains a chemiluminescent indicator. Receptacle 18 contains a hydrogen peroxide and color, and receptacle 19 contains an ester and color. Optionally, an absorbent and disbursing member 22 can be included on top of receptacles 18 and 19, as shown in FIG. 2. Here, disbursing member 22 is composed of felt. Receptacles 18 and 19, along with felt disburser 22, are housed inside cover 24, which is attached to base 12, as seen in FIG. 2. Cover 24 can be made from any plastic that possesses suitable characteristics of flexibility and durability. Here, cover 24 is manufactured from a semi-transparent and moderately flexible plastic.

When plastic receptacles 18 and 19 are broken in response to pressure, they release the chemiluminescent indicator, which then causes the patch 10 to emit light. Any chemicals that will emit chemical light as a result of their chemical reaction can be used in receptacles 18 and 19. Here, the chemicals are those used by Omniglow® Chemiluminescence and the emitted light is in the form of peroxyoxalate chemiluminescence.

Figure 3:
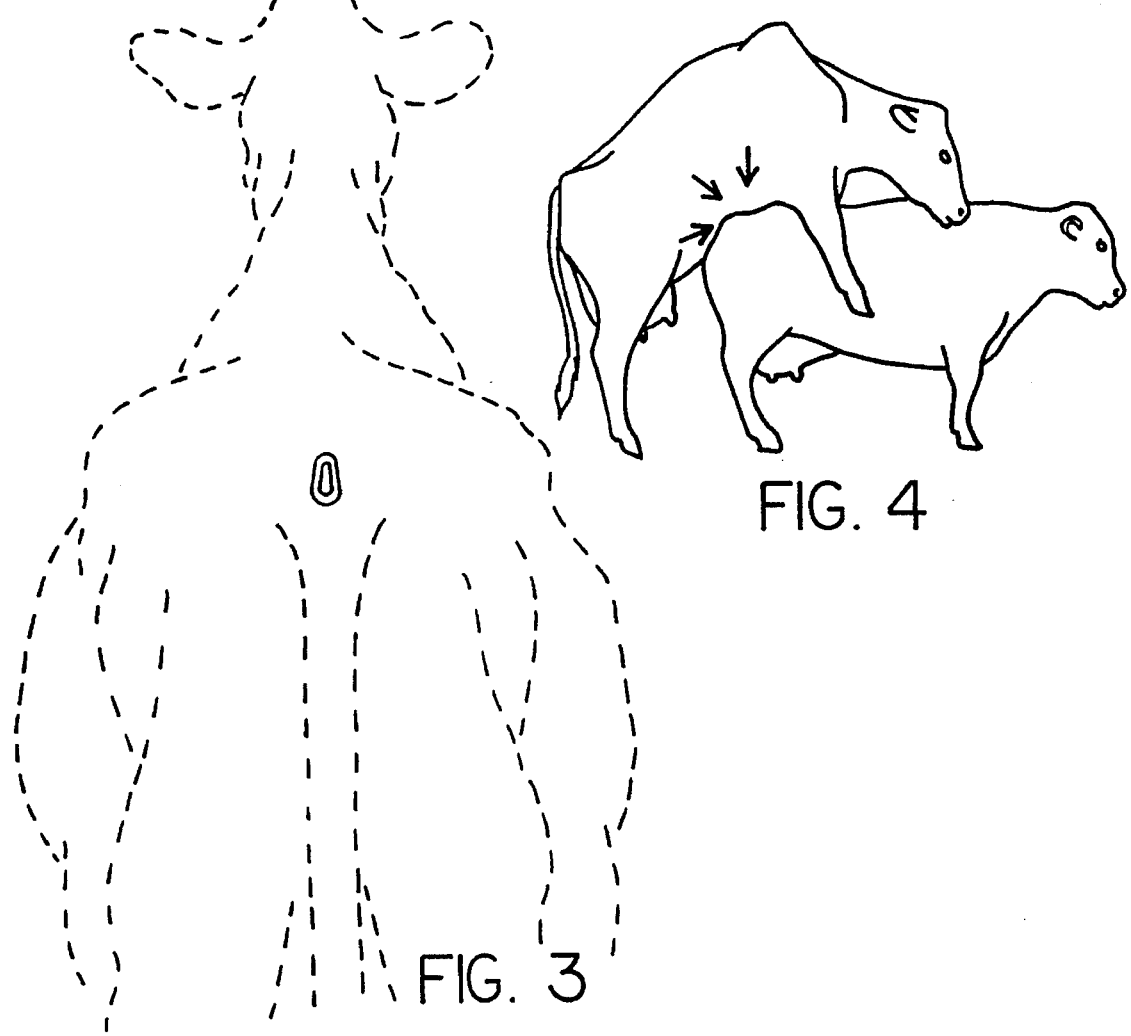
FIG. 3 is an environmental view showing placement of the detection device on the cow.
Figure 4:
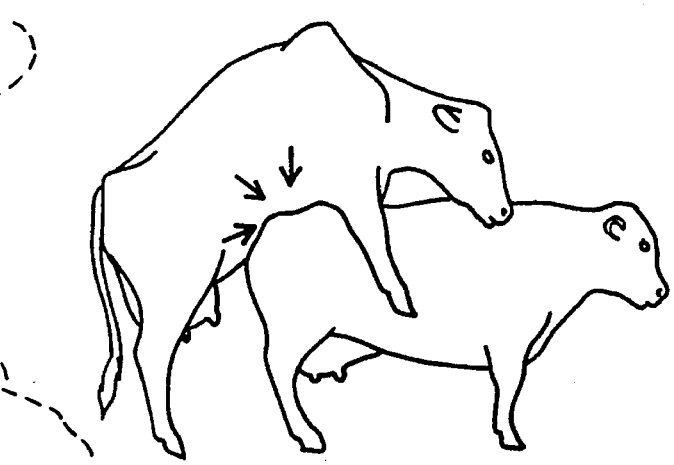
FIG. 4 is an environmental view showing the apparatus in use on the standing cow that is being mounted by the jumping cow.

In use, patch 10 is attached to the cow on bottom surface 12. Patch 10 is preferably attached to the cow on the dorsal midline, at approximately the tail head, or between the pelvic bones of the cow, as best seen in FIG. 3. Patch 10 can be attached to the cow by a self-adhesive attached to the canvas base of the patch or any other appropriate adhesive. Examples of adhesives that will work include the glues commonly used to attach sale tags to cattle at auctions or, any of the cyanoacrylate adhesives. After patch 10 is attached to the cow, receptacles 18 and 19 are broken in response to pressure, typically the result of the mounting of a second cow on top of patch 10 glued to the cow, as shown in FIG. 4. Upon breaking, the chemicals within receptacles 18 and 19 are commingled and chemically react, causing a chemical reaction which emits light. The reacted chemicals are drawn into felt 22 and thus disbursed across felt 22, which increases the visibility of the reaction. Felt 22 is often pressed in tight juxtaposition with cover 24 as a result of the pressure applied by the mounting cow on top of patch 10.

The chemical light released by the chemiluminescent indicator allows patch 10 to be seen more easily and from greater distances than would simply the release of a color paint. Additionally, the chemical light released from patch 10 allows patch 10 to be seen in the dark or in reduced daylight. Much of the monitoring of cows for estrus detection is done in the dark. For example, dairy cows are conventionally milked at 12 hour intervals. In most regions at least one of the milkings is usually done in the dark and one milking is during daylight. In some areas that have very short day lengths, it is not uncommon for both milkings and both gatherings of the cows to take place in the dark. With the release of the chemical light from patch 10, the behavioral estrus or standing for mounting behavior of the cow can be observed, even in the dark, when the cows themselves are still difficult to visually discern.

The peroxyoxalate chemiluminescence used in the preferred embodiment of this invention can be formulated in any color desired. This invention includes a method for managing the reproductive cycle of the cow, utilizing chemiluminescent patch 10.

The management method utilizes the fact that patch 10 can be manufactured in any color desired. In the management method of this invention, each different color of patch 10 indicates a particular breeding management status and scheme for a cow. The appropriate color of patch 10 is selected from a plurality of colors available for patch 10. In the preferred embodiment, patch 10 is manufactured in six different colors. Any colors that are easily discerned from each other, for example, a very deep yellow and a very pale yellow, can be used in this management scheme. Examples of colors that can be employed include: blue, red, orange, florescent green, lavender, yellow, green and magenta.

The management scheme or method consists of selecting the appropriate color patch to match the reproductive status of the cow. Secondly, the patch is applied to the cow, and thirdly, the cows to which the patches have been applied are observed and monitored for visualization of release of the indicator substance from receptacles 18 and 19 within cover 24 on patch 10.

The first color selected, for example blue, of patch 10 can be applied to the cow at the time of calving. This patch, when discharged, will indicate that the cow is showing a first post-partum estrous cycle. From the discharge of this patch, the management information that can be gathered is the average length of the cow's cycle since calving, as well as a timely check of whether or not the cow's reproductive tract has returned to a condition appropriate for rebreeding or if the cow is in need of therapeutic attention.

At the time the cow is brought in for the discharge of the first color patch, that first patch can be removed and a second selected color of patch 10, for example red, is applied to the cow's tail head area. The second color of patch 10 identifies the cow's reproductive status as having been artificially inseminated after that first post-partum estrous cycle and having not yet shown behavior of another estrous cycle.

If the second color of patch 10 is discharged, the cow is brought back in and a third selected color of patch 10 is applied to the cow's tail head area. The third color, for example orange, identifies the cow's status as having been artificially inseminated during the first post-partum estrous cycle and having returned to estrus after that breeding. Cows wearing the third color of patch 10 can be identified as either having been reinseminated or therapeutically treated for any reproductive health problems at the time of application of the third color of patch 10.

A fourth selected color of patch 10, for example yellow, can be applied to the cow after the discharge of the first color of patch 10, if, at the time this cow is brought back in, this cow was not inseminated, but rather, therapeutically treated. The information gathered from the discharge of this fourth color of patch 10 is the length of the estrous cycle after therapeutic treatment, this provides the opportunity to either artificially inseminate the cow at this time or re-evaluate her reproductive status for possible further therapeutic treatment or culling from the herd.

A fifth selected color of patch 10, for example green, can be used on the cow to indicate that the current estrous cycle is other than the first post-partum estrous cycle; that is, the second or greater estrous cycle post-partum, and that this cow has been artificially inseminated during more than one estrous cycle. Discharge of this fifth color of patch 10 would indicate that the cow has again been unsuccessfully bred after more than one insemination and multiple estrous cycles.

A sixth selected color of patch 10, for example magenta, can be applied to the cow's tail head area to indicate that the cow is in an estrous cycle other than the first post-partum estrous cycle and that this cow has not been artificially inseminated, but is being maintained with a bull for natural service. The reproductive status information that can be gathered from the discharge of this sixth color of patch is that this cow has been naturally serviced by the bull.

While there is shown and described the present preferred embodiment of the invention, it is to be distinctly understood that this invention is not limited thereto but may be variously embodied to practice within the scope of the following claims.

I claim:

1. A method for managing the reproductive status of cows comprising:

selecting a pressure responsive estrus detection patch from a plurality of color patches wherein each color of patch indicates a particular breeding management status for the cow from a group consisting of:
  a) a first color of patch identifying a cow's status as being in the interval between
    1) parturition and
    2) first post-partum estrous cycle;
  b) a second color of patch identifying a cow's status as being artificially inseminated and in the interval between
    1) first post partum estrous cycle and
    2) next estrous cycle;
  c) a third color of patch identifying a cow's status as being in the interval between
    1) having been artificially inseminated in the first post partum estrous cycle and showing a next estrous cycle after the insemination and having received selective management, wherein the selective management choice is from the group consisting of re-insemination and therapeutic treatment; and
    2) the next estrous cycle after treatment or re-insemination;
  d) a fourth color of patch identifying a cow's status as being in the interval between
    1) the first post partum estrous cycle, having received treatment without insemination and
    2) the next estrous cycle;

e) a fifth color of patch identifying a cow's status as being in the interval between
   1) an estrous cycle other than first post partum and having been artificially inseminated during a plurality of estrous cycles and
   2) the next estrous cycle since last breeding;
f) a sixth color of patch identifying a cow's status as being in the interval between
   1) an estrous cycle without artificial insemination and
   2) being maintained with a bull for natural mating;

attaching the selected color of patch to the cow near the dorsal midline between the pelvis and tailhead of the animal; and observing and monitoring the cows for release of the indicator substance contained in the patch in response to pressure from mounting.

2. The method for managing the reproductive status of cows of claim 1 wherein the pressure responsive estrus detection patch contains a chemiluminescent indicator.

3. A method for managing the reproductive status of an animal comprising:

providing a plurality of different color, pressure-responsive estrous detection devices wherein each color of device indicates a particular breeding management status for the animal, attaching a selected device to the animal at a location adapted to detect mounting activity, and observing and monitoring the pressure-responsive device on the animal for an indication of mounting activity in response to pressure created by mounting.

4. The method of claim 3 wherein the pressure-responsive devices contain a chemiluminescent indicator.

5. The method of claim 3 wherein the attaching of the device is done near the dorsal midline between the pelvis and the tailhead of the animal.

6. The method of claim 3 wherein the animal is a cow.

7. The method of claim 3 wherein the devices comprise:

a first color device identifying the animal's status as being in the interval between
   1) parturition and
   2) first post-partum estrous cycle.

8. The method of claim 7 wherein the devices further comprise:

a second color device identifying the animal's status as having been artificially inseminated and in the interval between
   1) first post-partum estrous cycle and
   2) next estrous cycle.

9. The method of claim 8 wherein the devices further comprise:

a third color device identifying the animal's status as being in the interval between
   1) having been artificially inseminated in the first post-partum estrous cycle and showing a next estrous cycle after the insemination and having received selective management, wherein the selective management choice is from the group consisting of re-insemination and therapeutic treatment; and
   2) the next estrous cycle after treatment or re-insemination.

10. The method of claim 9 wherein the devices further comprise:

a fourth color device identifying an animal's status as being in the interval between
   1) the first post-partum estrous cycle, having received treatment without insemination and
   2) the next estrous cycle.

11. The method of claim 10 wherein the devices further comprise:

a fifth color device identifying an animal's status as being in the interval between
   1) an estrous cycle other than the first post-partum and having been artificially inseminated during a plurality of estrous cycles and
   2) the next estrous cycle since last breeding.

12. The method of claim 11 wherein the devices further comprise:

a sixth color device identifying an animal's status as being in the interval between
   1) an estrous cycle without artificial insemination and
   2) being maintained with a bull for natural mating.

* * * * *